United States Patent [19]

Fenwick

[11] Patent Number: 5,445,165
[45] Date of Patent: Aug. 29, 1995

[54] MEDICAL DRAPE WITH DRAIN AND METHOD FOR DEPLOYING

[75] Inventor: Robert C. Fenwick, Cincinnati, Ohio

[73] Assignee: Liebel-Flarsheim Company, Cincinnati, Ohio

[21] Appl. No.: 15,785

[22] Filed: Feb. 10, 1993

[51] Int. Cl.6 .......... A61B 19/00; A61B 19/08
[52] U.S. Cl. ................ 128/849; 128/853
[58] Field of Search .............. 128/849–856

[56] References Cited

U.S. PATENT DOCUMENTS

| 3,030,957 | 4/1962 | Melges | 128/853 |
|---|---|---|---|
| 3,236,370 | 2/1966 | Pereny et al. | |
| 3,677,266 | 7/1972 | Green | 128/853 |
| 3,856,006 | 12/1974 | Krzewinski | |
| 3,862,632 | 1/1975 | Hirsch | 128/853 |
| 3,892,617 | 7/1975 | DePriest et al. | |
| 3,942,523 | 3/1976 | Rudtke | |
| 4,007,741 | 2/1977 | Waldrop et al. | |
| 4,059,104 | 11/1977 | DePriest | 128/853 |
| 4,081,306 | 3/1978 | DePriest | 128/853 |
| 4,378,794 | 4/1983 | Collins | |
| 4,414,968 | 11/1983 | Amin | 128/853 |
| 4,462,396 | 7/1984 | Wichman | |
| 4,471,769 | 9/1984 | Lockhart | |
| 4,690,137 | 9/1987 | Starzmann | |
| 4,890,628 | 1/1990 | Jackson | |
| 4,903,710 | 2/1990 | Jessamine et al. | |
| 5,002,070 | 3/1991 | Taylor | 128/853 |
| 5,029,243 | 5/1993 | Glassman | 128/853 |

Primary Examiner—Michael A. Brown
Attorney, Agent, or Firm—Wood, Herron & Evans

[57] ABSTRACT

The present invention is a medical drape having at least one sheet with an upper and a lower fenestration formed therethrough, a screen filter and a drainage bag affixed over the lower fenestration, and a hose having one end in fluid communication with the drainage bag. Preferably, the drape is generally I-shaped.

35 Claims, 4 Drawing Sheets

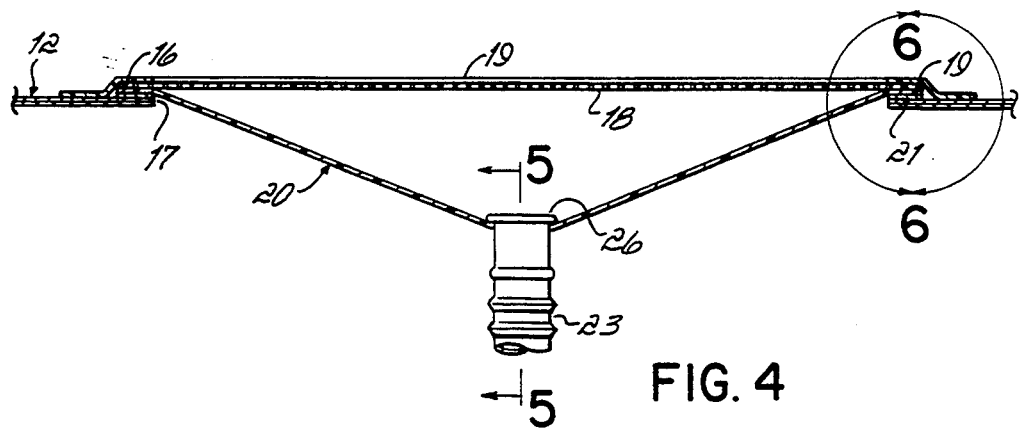
FIG. 4
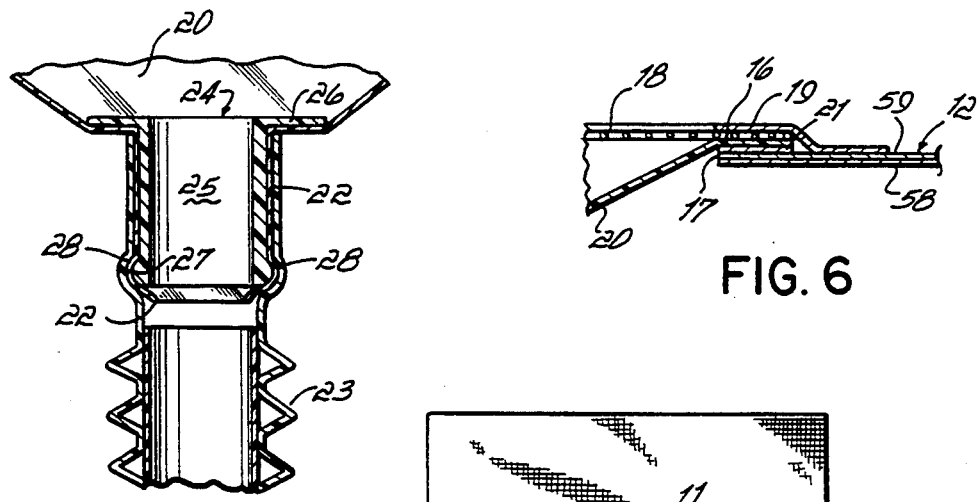
FIG. 5
FIG. 6
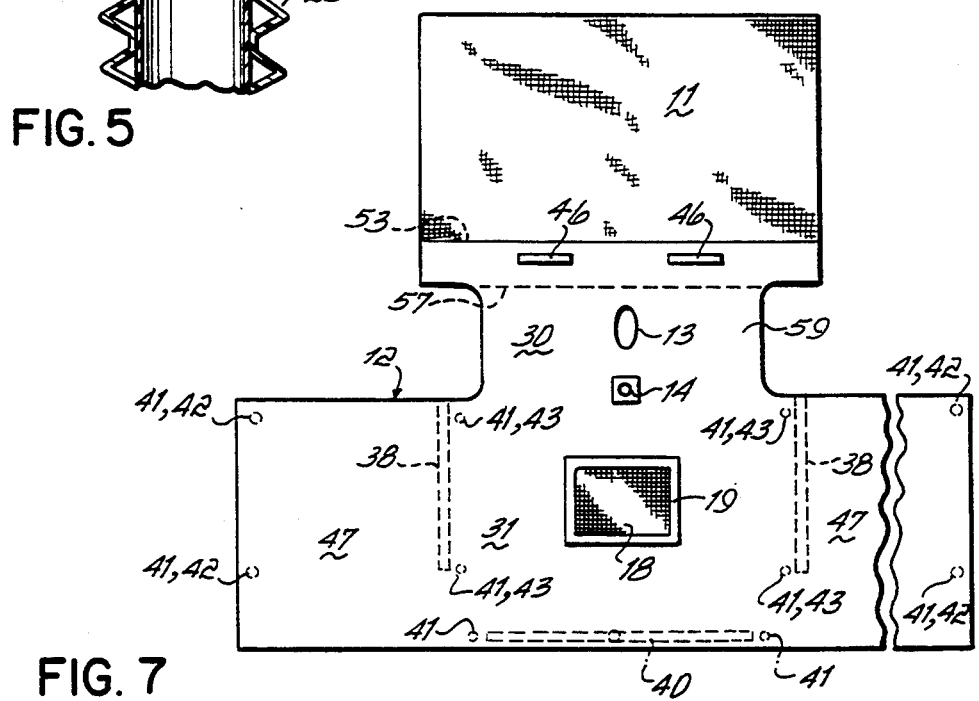
FIG. 7

MEDICAL DRAPE WITH DRAIN AND METHOD FOR DEPLOYING

FIELD OF THE INVENTION

This invention relates to medical drapes, and more particularly, it relates to disposable urology and gynecological drapes and a method for deploying same.

BACKGROUND OF THE INVENTION

Medical drapes have been used in a variety of applications. For example, such drapes are often used to cover a patient during an operating procedure. These drapes come in a variety of styles and configurations to meet the requirements of particular operating procedures and are typically disposable. In general, such drapes include a sheet provided with an opening or fenestration through which a physician can gain access to a patient (i.e., the operating site). Drapes used for urological applications, such as cystoscopy or Trans Uretheral Resection of the Prostate (T.U.R.P.), are generally shaped in the form of a "T". During urological procedures, the patient is typically in a reclined position with raised knees. The top horizontal section (i.e., abdominal cover) of the T-shaped sheet is draped across the patient's torso and the lower vertical section (i.e., T-section) of the sheet falls between the patient's legs. At least one fenestration is located in the T-section through which the operating procedure is performed. When urological procedures such as cystoscopy or T.U.R.P. are to be performed, a filter formed in the T-section is used to separate out solids from liquid expelled by the patient. One type of filter generally used includes a fine screened filter covering a second fenestration formed in the T-section. U.S. Pat. No. 4,059,104 discloses such a urology T-drape.

Tables used during urological procedures often include a drain frame mounted to the foot of the table. A separate drainage bag is secured to the drain frame. One end of a hose is typically fixed to the drainage bag with the other end of the hose connected to some form of receptacle, like a reservoir or a sewer drain. The hose is often connected by inserting the other end into an opening in the reservoir or into the sewer drain. The patient is positioned on the table such that when the patient is covered with the T-drape, the filter portion of the T-section is positioned over the drainage bag. Liquids expelled from the patient are intended to flow from the first fenestration down over the drape to and through the second fenestration and into the drainage bag. From there the liquid passes through the hose and is collected in the reservoir or drained to the sewer. The end of the hose is susceptible to being inadvertently pulled out of the reservoir opening or sewer drain. The hose would thus have to be re-connected to the reservoir or sewer drain. In addition, the liquid expelled from the patient could end up flowing onto the floor of the operating room or elsewhere.

Drain frames are traditionally considered nonsterile. Therefore, someone other than the physician typically attaches the drainage bag to the frame. Drapes, on the other hand, are traditionally considered sterile. Thus, after the drainage bag has been attached to the frame, the physician can unfold and deploy the drape over the patient as previously described without the risk of becoming nonsterile. Such procedures would be less expensive if the need for someone other than the physician to assemble the drainage system could be avoided.

During such urological and other medical procedures, it is important to capture as much of the fluid expelled from the patient as possible. One reason is to protect the physician and the medical support personnel from the expelled fluid. With the spread of the AIDS virus, the need to contain the expelled bodily fluids of a patient and cleaning-up after such procedures takes on even greater importance today. Another reason is to insure that all the expelled fluid is screened in order to capture any expelled solids for further examination. Capturing more of the expelled fluid also makes clean-up after the procedure easier, less time consuming and more cost effective. Cleaning-up the operating room faster enables more operating procedures to be performed in a given time.

SUMMARY OF THE INVENTION

It is an object of the present invention to provide a medical drape which eliminates the need for a separate drainage bag.

Another object of the present invention is to provide such a medical drape which can be deployed by a physician without risk of contamination from nonsterile portions of the operating table, in particular the drain frame mounted at the foot of the table.

An additional object of the present invention is to provide a medical drape which is likely to capture more of any fluid expelled by a patient during an operating procedure.

A further object of the present invention is to provide a medical drape which eliminates the need for a separate drainage receptacle.

In accordance with the present invention, a medical drape is provided having an upper sheet section and a lower sheet section. An upper and a lower fenestration are formed through the lower sheet section of the drape. A filter is affixed over the lower fenestration. A drainage bag is also affixed over the lower fenestration. One end of a hose is in fluid communication with the drainage bag. By fixing the drainage bag to the drape in this manner, the need for a separate drainage bag and a person other than the physician to attach the drainage bag to the drain frame is eliminated. The physician can now deploy both the medical drape sheet and drainage bag without becoming nonsterile.

To help ensure that liquids expelled from a patient and funneled through the drainage bag will reach an appropriate receptacle, the present drape can be provided with a receptacle pre-attached to the free end of the drainage hose.

To facilitate the deployment of the medical drape while maintaining the sterility of the physician, the present drape is intended to be completely sterile and packaged with the sheet folded, the bag folded on top of the sheet, and the hose coiled on top of the bag. If the drainage receptacle is pre-attached, it would be positioned on top of the coiled hose. The drape is then packaged in this condition. Preferably, the folded drape is banded with a paper tape before packaging. The drape is deployed by first removing the packaging, orienting the folded drape with the bag, hose, and, if pre-attached, the receptacle below the folded sheet, and positioning the folded drape over the drain frame on the table. The paper band is then ripped in two, dropping the receptacle, if pre-attached, the hose and bag through the frame. Finally, the drape sheet is unfolded over the patient and the table. This packaging and bomb site deployment method of the present drape further insures that the physician can install the drainage bag as well as apply the sheet without fear of becoming non-sterile. While the above deployment procedure is preferred, it is understood that various acceptable methods of packaging and deployment of the present drape are possible.

In another aspect of the present invention, a generally I-shaped drape is provided, as opposed to the T-shaped drapes prevalent in the prior art. The lower sheet section of the I-shaped drape has an upper portion with two side edges and a lower portion with two side edges and a bottom edge. The upper portion is narrower than either the lower portion or the upper sheet section. The narrow upper portion of the lower sheet section is preferably comparable in width to the vertical T-section found in most commercially available prior art T-shaped urology drapes. The lower fenestration is positioned within the lower portion of the lower sheet section. Therefore, because it is wider, the lower portion of the present drape can be formed into a larger funnel shape than the vertical T-section of prior art T-shaped drapes. Any fluid expelled from the patient during the operating procedure would, thus, be more likely captured and its flow directed toward and through the screened filter. Toward this end, it is contemplated to make the side edges of the wide lower portion securable to the patient's legs in order to form the desired funnel shape, for example, with adhesive strips, snaps, or the like. The lower portion of the lower sheet section can also be made wide enough to drape over the bent legs of the patient with or without such adhesive strips, snaps, etc.

Not all operating tables include a drain frame suitable for receiving the drainage bag. Some tables utilize a removable pan rather than the drain frame and drainage bag combination. Therefore, it may not be feasible to use the present drape and drainage bag combination with such a table. Under these circumstances, it is still advantageous to use the generally I-shaped drape of the present invention even without the drainage bag being attached thereto.

The above and other objects, features and advantages of the present invention will become more apparent upon consideration of the following description taken in conjunction with the accompanying drawings.

BRIEF DESCRIPTION OF THE DRAWINGS

FIG. 4 is a sectional view taken along lines 4—4 of FIG. 2;

FIG. 5 is a sectional view taken along lines 5—5 of FIG. 4;

FIG. 6 is an enlarged view taken from the encircled portion 6—6 of FIG. 4;

FIG. 7 is a top planar view of a modification of the drape of FIG. 1;

DETAILED DESCRIPTION OF THE INVENTION

Figures 1, 8:
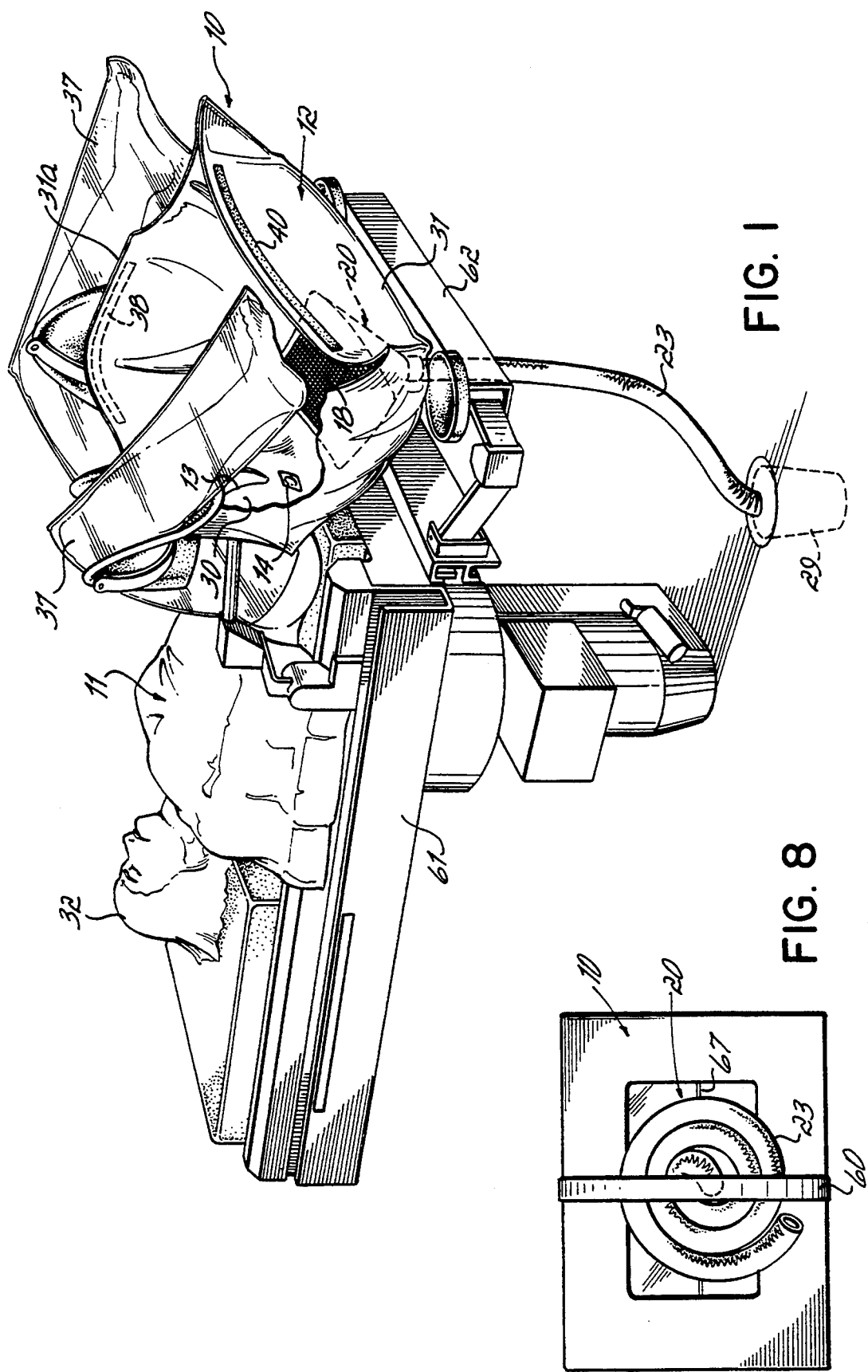
FIG. 1 is a perspective view of one embodiment of the present drape in a deployed condition.
FIG. 8 is a top view of the drape of FIG. 1 in a preferred folded condition.
Figure 2:
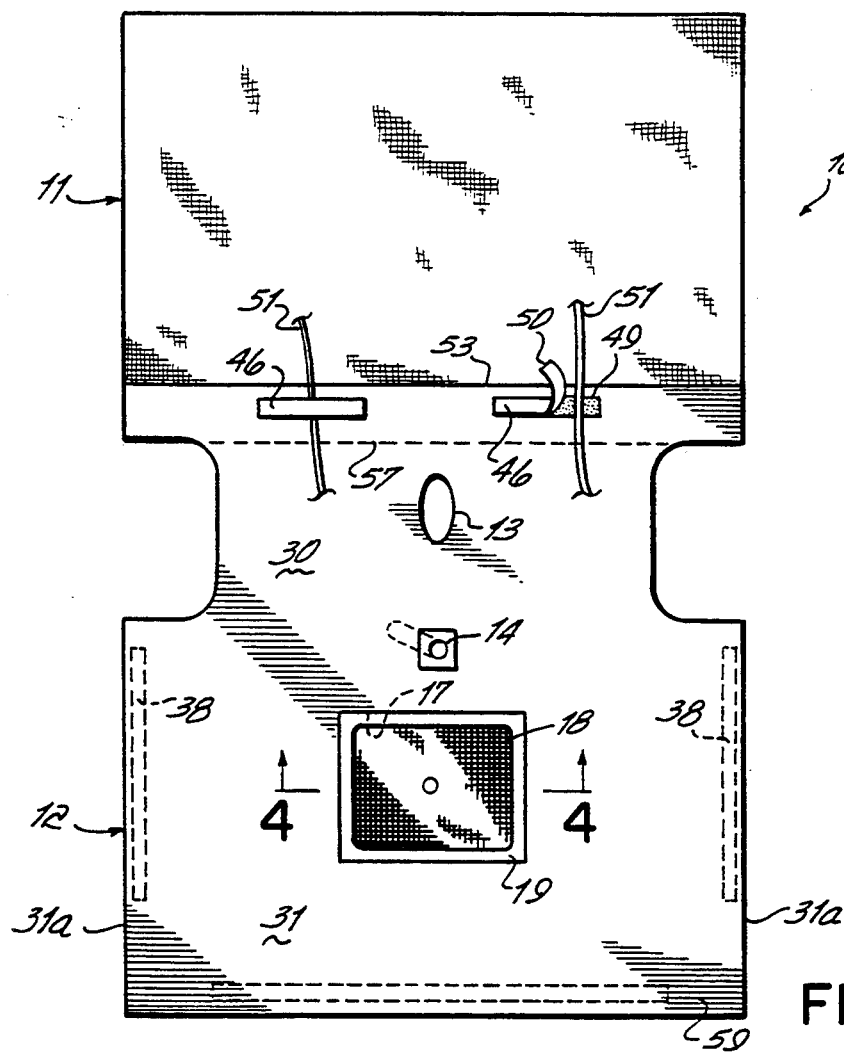
FIG. 2 is a top view of the drape of FIG. 1 in an unfolded and spread out condition.

Referring to FIGS. 1 and 2, a disposable urology drape 10 according to the present invention is shown which includes an upper sheet section 11 and a lower sheet section 12. An upper fenestration 13 and a lower fenestration 17 are formed through the lower sheet section 12 of the drape 10. Optionally, a finger cot 14 can be fixed to the lower sheet section 12 between the fenestrations 13, 17 to provide sterile access to the patient. A screen filter 18, which is well known in the art, is affixed to the lower sheet section 12 over the lower fenestration 17 with a frame of adhesive tape 19, for example, a polyethylene tape coated on one side with pressure sensitive hypoallergenic acrylate adhesive, manufactured by 3M, St. Paul, Minn., product no. 1525-L. Preferably, the tape is about 1" wide.

Figure 3:
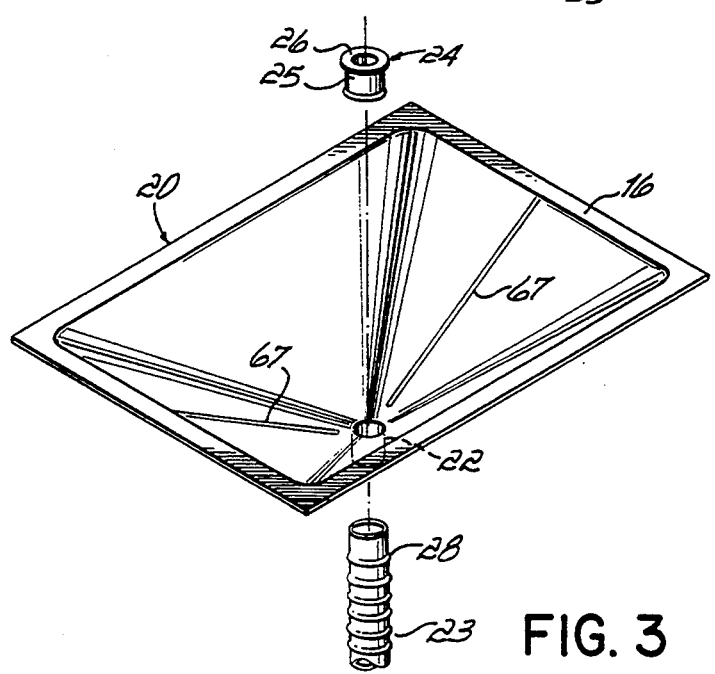
FIG. 3 is an exploded perspective view of a drainage bag and hose according to the present invention.

Referring to FIGS. 3, 4 and 6, a plastic drainage bag 20, preferably made of polyethylene plastic material, has a lip 16 formed around its rim. The bag 20 is affixed over the lower fenestration 17 with a frame of double sided adhesive tape 21, for example, a transparent polyethylene tape coated on both sides with a hypoallergenic pressure sensitive acrylate adhesive, also manufactured by 3M, part no. 1509. The lip 16 of the drainage bag 20 is positioned between the screen filter 18 and the lower sheet section 12. The tape 21 is sandwiched between the underside of the lip 16 and the lower sheet section 12 around the lower fenestration 17.

Referring to FIGS. 3–5, the drainage bag 20 is generally funnel shaped with an exit spout 22 formed at its lower end. The exit spout 22 is sealed to one end of a hose 23. A hose connector 24 is intended to be press fit into the exit spout 22 to form a frictional seal between the exit spout 22 and the one end of the hose 23. The exit spout 22 is thus sandwiched between the hose connector 24 and the one end of the hose 23. The hose connector 24 has a short tubular section 25 with a through bore. The tubular section 25 has a ring shaped flange 26 at its trailing end and a circumferential rib 27 formed adjacent to its leading end. When the hose connector 24 is press fit into the exit spout 22, the rib 27 engages and interlocks with a matching groove 28 formed in the one end of the hose 23. The exit spout 22 is intended to be compressed between the rib 27 and groove 28 in order to form a frictional seal. However, it may be necessary to adhere a portion of the drainage bag 20 to the flange 26, for example, by using an adhesive glue or fusing the two together with a hot melt process. The other end of the hose 23 is in fluid communication with some form of drainage receptacle 29, such as a reservoir or a sewer drain for receiving bodily fluids expelled from the patient as shown in FIG. 1.

Figure 10:
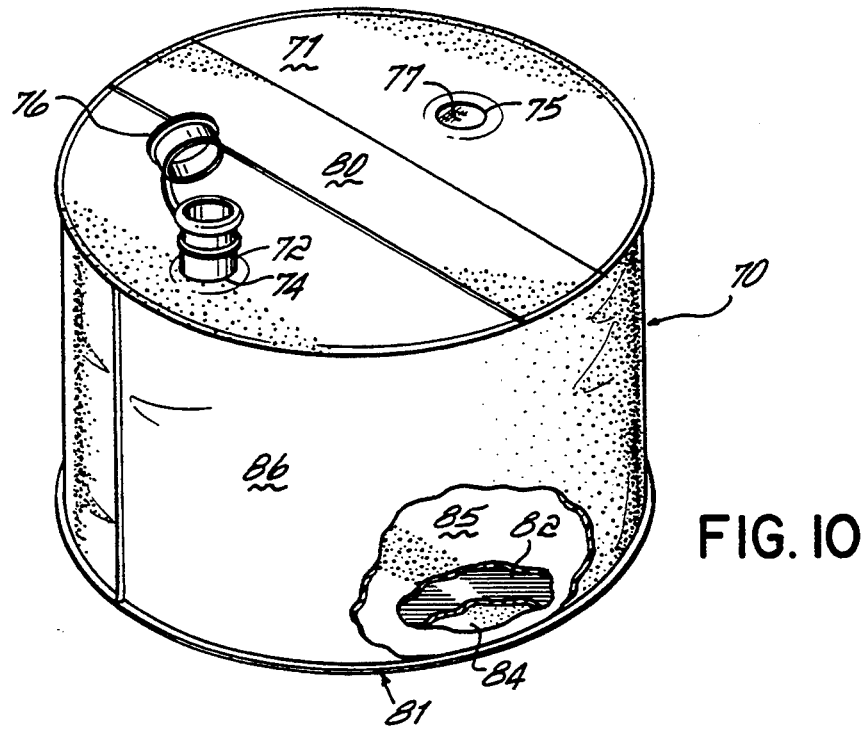
FIG. 10 is a partially broken away perspective view of a drainage receptacle according to the present invention.

Referring to FIG. 10, the drainage receptacle 29 can be a collapsible bucket or bag which is pre-attached to the other end of hose 23. The collapsible bucket 70 is preferably made with a shell of polyethylene plastic material and has a top layer 71 with a hose connector 72, similar to hose connector 23, integral therewith. The connector 72 is adhered to the top layer 71, preferably with a hot melt process, inside an entrance opening 74 in the top 71. The connector 72 is either press fit or adhesively bonded into the other end of hose 23 in the manner shown in FIG. 5 for attaching the connector 24 to the one end of the hose 23, except that the exit spout 22 is not present. A removable cap 76, attached to connector 72, can be used to seal the end of connector 72 when the hose 23 is disconnected from the connector 72. In order to facilitate the displacement of air as expelled fluids enter the bucket 70, a vent opening 75 is also formed through the top layer 71 of the bucket 70. The vent 75 is preferably covered over with a membrane 77 which allows air to flow therethrough but tends to prevent the passage of fluids. Such a membrane 77 is manufactured under the tradename Versapel, No. 1200, by a company named Gelman Sciences in Ann Arbor, Mich.

A strap 80 is positioned across the top 71 of the bucket 70 with the ends of the strap 80 fixed to opposite edges of the top 71. The strap 80 facilitates carrying the bucket 70, particularly when the bucket is full of fluids. The bucket 70 has a triple layer bottom 81 which includes a layer of cardboard 82 sandwiched between two layers of polyethylene plastic material 84 and 85. The layer of cardboard 82 helps to maintain the shape of the bucket 70. The bucket 70 has a side wall layer 86 which is collapsible to facilitate packaging of the drape 10. Optionally, a jelling powder (not shown), such as that manufactured by Isolyser in Norcross, Ga., can be placed inside the bucket 70 to turn the expelled liquids into a jell. With the expelled liquid in the form of a jell, the likelihood of inadvertent contamination is reduced. A collapsible bucket 70 like the one described above is presently being manufactured by Gold Medal in Richmond, Va., part No. 601012.

The drape 10 preferably has a generally I-shape, with the lower sheet section 12 having an upper portion 30 and a lower portion 31 (see FIG. 2). The lower portion 31 of the lower sheet section 12 is comparable in width to the upper sheet section 11, typically about 53 inches wide. The upper portion 30 of the lower sheet section 12 is narrower than either the lower portion 30 or the upper sheet section 11 and comparable in width to the vertical T-sections found in most commercially available prior art T-shape urology drapes (not shown), typically about 36 inches wide. The narrow upper portion 30 gives the drape 10 its I-shape. The lower fenestration 17 is formed through the lower portion 31 of the lower sheet section 12 and the upper fenestration 13 is formed through the upper portion 30 of the lower sheet section 12.

The side edges 31a of the lower portion 31 are preferably attachable to the legs of a patient 32, and the bottom edge of the lower portion 31 is preferably attachable to the chest or abdomen of an attending physician (not shown), in order to form the lower portion 31 into a funnel shape (see FIG. 1). Normally, the patient 32 wears leggings 37 over each leg. Preferably, at least one adhesive strip 38, such as the previously described 3M double coated tape, part no. 1509, is fixed to the underside of the drape 10 along either side edge 31a of the lower portion 31 for attachment to the leggings 37. At least one adhesive strip 40, such as the same 3M, 1509 double coated tape, is fixed to the underside of the drape 10 along the bottom edge 31b of the lower portion 31 for attachment to the front of the physician.

Referring to FIG. 7, in a modification of the preferred drape 10, the lower portion 31 can be widened with extended portions or wings 47 in order to drape over and preferably around the bent legs of the patient 32. Adhesive strips 38 or, alternatively, a plurality of snaps 41 having two pieces 42, 43 (shown in phantom), for example, PVC molded snaps manufactured by Cosmos, Long Island, N.Y., could be used to secure the extended portion 47 of the widened lower portion 31 around the patient's legs. Such an arrangement would likely eliminate the need for the leggings 37. The snaps 41 could also be used instead of any of the adhesive strips 38 and 40. When used instead of the adhesive strip 40, one piece 42 (shown in phantom) of a plurality of snaps 41 would be fixed along the bottom edge 31b of the lower portion 31, and the other piece (not shown) of the snaps 41 would be fixed to the physician's clothing. If snaps 41 are used instead of the adhesive strips 38 on the embodiment of drape 10 shown in FIG. 2, one piece 42 (shown in phantom) of a plurality of the snaps 41 would be fixed along the side edges 31a of the lower portion 31, and the other piece (not shown) of the snaps 41 would be fixed to the leggings 37.

At least one, and preferably two holders 46, manufactured by Custom Medical Products, Asheville, N.C. under the tradename Soft Grip tube holder, are fixed to the upper surface of the drape 10 above the narrow upper portion 30 and on either side of the upper fenestration 13. Each holder 46 includes a strip of reapply adhesive tape 49 with a plastic cover strip 50. These holders 46 are used to hold such things as tubes 51 and cords 52 used during the urological procedure. The tubes 51 or cords 52 are trapped between the plastic cover strip 50 and the reapply adhesive strip 49 of the holders 46 (see FIG. 2).

Presently, the upper sheet section 11 and the lower sheet section 12 begin as two separate pieces which are adhesively bonded along overlapping margins 53, 57, respectively, in any suitable manner well known in the art, for example with the previously described 3M, 1509 double coated tape. The upper sheet section 11 is made of a nonwoven fabric material. An example of a preferred material is a wood pulp polyester spun lace material with a water repellent treatment, manufactured by Precision Fabrics Group, Inc., Greensboro, N.C., under the tradename Sontara, style no. 097-08818. The lower sheet section 12 is a 2-ply laminate of a nonwoven fabric material 58 coated with a plastic film 59. (See FIG. 6.) An example of a preferred laminate is a thin 2.5 mil thick film layer of a polyethylene extrusion which is adhesive laminated by Clopay, Cincinnati, Ohio, to a layer of 1.25 ounce nonwoven polyester spun lace material, manufactured by Kimberly-Clark, Roswell, Ga. under the tradename spun bond. During urological procedures, high intensity lights are typically used to illuminate the operating area. The polyethylene coating 59 is preferably textured with a pattern to reduce glare from these bright lights.

The spun lace material provides the upper sheet section 11 with the feel of a normal blanket for the patient's comfort. Operating rooms are typically kept relatively cool and patients are usually not heavily clothed during the operation. Therefore, the upper sheet section 11 is also intended to keep the patient warm during the procedure. However, the water repellent spun lace material used to make the upper sheet section 11 is significantly more expensive than the 2-ply laminate material used to make the lower sheet section 12. In addition, because of its polyethylene coating 59, the 2-ply laminate material used to make the lower sheet section 12 would likely keep the patient warmer than the single ply of spun lace material used to make the upper sheet section 11. Therefore, it is contemplated to make the entire drape 10 out of the 2-ply laminate material rather than just the lower sheet section 12.

Figure 9:
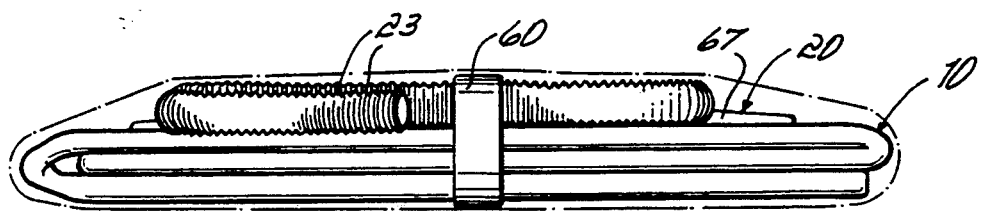
FIG. 9 is a side view of the folded drape of FIG. 8.
Figure 11:
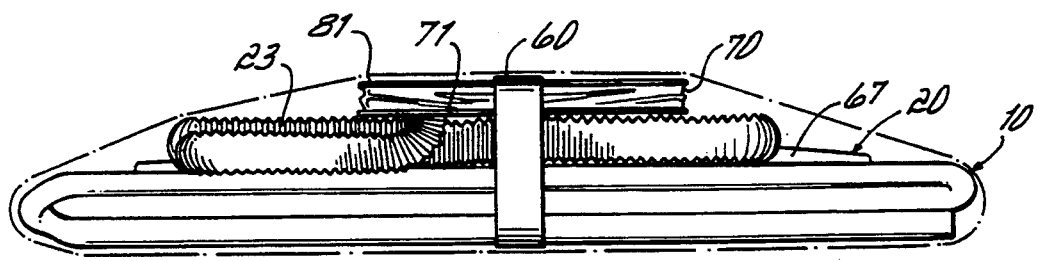
FIG. 11 is a side view of the drape of FIG. 1 with the drainage receptacle of FIG. 10 pre-attached to the drainage hose.

Referring to FIGS. 8, 9 and 11, to facilitate the deployment of the present urology drape 10 while maintaining the sterility of the physician, the drape 10 is intended to be completely sterile and packaged with the sheet sections 11, 12 folded in any acceptable manner over the screen filter 18 with the drainage bag 20 left exposed. The drainage bag 20 is then collapsed on top of the folded sheet sections 11, 12, and the hose 23 coiled on top of the drainage bag 20. If present, the bucket 70 is then collapsed and positioned on top of the coiled hose (see FIG. 11). The folded drape 10 is then preferably banded with a paper tape 60 and then packaged in industry standard packaging. The preferred embodiment of the present drape 10 is intended to be used with a urology table 61 which includes a drain frame 62 mounted to the foot of the table 61. One such drain frame 62 is disclosed in U.S. Pat. No. 4,936,836 which is assigned to the assignee of the present invention and incorporated by reference herein in its entirety. In the past, a separate drainage bag (not shown) was secured to the drain frame 62.

The drape 10 is preferably deployed by first removing the packaging, orienting the folded drape 10 with the bag 20, hose 23, and, if pre-attached, the bucket 70 below the folded sheet sections 11, 12, and then positioning the folded drape 10 over the drain frame 62. The paper band 60 is then ripped in two, dropping the bucket 70, if pre-attached, hose 23 and bag 20 through the drain frame 62. Finally, the sheet sections 11, 12 are completely unfolded. In no particular order, the bottom edge 31b and side edges 31a of the lower portion 31 of the lower sheet section 12 are secured to the physician (not shown) and the patient 32, respectively, as previously described. By having the bucket 70 attached to the other end of the hose 23 as described above, the physician or other medical personnel do not have to worry about inserting the hose 23 into the receptacle 29.

With the drape 10 fully deployed, bodily fluids expelled from the patient 32 which pass through the upper fenestration 13 are funneled toward and through the lower fenestration 17 and into the drainage bag 20. Expelled solids are separated out by the filter 18. Once in the bag 20, the expelled fluids flow toward the exit spout 22, through the tubular section 25 of the hose connector 24, and finally through the hose 23 in order to drain into either the reservoir 29 or the bucket 70. The hose 23 is preferably corrugated with a smooth inside diameter. An example of a suitable hose is manufactured by Smooth-Bor, Laguna Hills, Calif., product no. 103-72. Corrugated hose is preferred because the corrugations provide structural strength against the hose collapsing and thereby blocking the flow of expelled fluid to the reservoir 29. The inside diameter of the hose 23 is preferably smooth to prevent the expelled fluids passing through the hose 23 from pooling inside the corrugations, and thereby making clean up more difficult. In addition, the expelled fluids are sometimes themselves the subject of analysis. A corrugated inside diameter would make it more difficult to secure these fluids for analysis.

The packaging and bombsight deployment method of the present invention helps to insure that the physician can install the drainage system (i.e., the bag 20, hose 23, and, if present, the bucket 70) and apply the sheet sections 11, 12 without fear of becoming nonsterile. While the above packaging and deployment method is preferred, it is understood that alternative equivalent methods are possible which would accomplish the same results. For example, the drape 10 could be folded with the bag 20, hose 23 and, if present, the bucket 70 enclosed within the folded sheet sections 11, 12. The drape 10, folded in this manner, would then be placed on the patient and unfolded such that the bag 20, hose 23 and, if pre-attached, bucket 70 still drop through the drain frame 62, though the drape 10 would not be bombsight deployed.

As disclosed in the U.S. Pat. No. 4,936,836 patent, the drain frame 62 has pivotally interconnected parts that are vertically rigid, yet moveable in a horizontal direction to varyingly distort the configuration of the frame 62. That is, the frame 62 is moveable from side to side and collapsible towards the table 61. Because of the moveability of the drain frame 62, the lower portion 31 of the sheet section 12 around the screen 18 is preferably securable to the frame 62 in order to insure that the bag 20 remains within the frame 62. The lower portion 31 can be secured to the frame 62 by using fasteners cooperable with the frame structure. For example, two piece snaps like snaps 41 could be used, with one piece fixed to the lower sheet section 12 and the other piece fixed to the frame 62, or adhesive strips like strips 38, 40 fixed to the sheet section 12 for adhesion to the frame 62. A transverse crease 67 is preferably formed along the bottom of the bag 20 so that the bag 20 easily folds as the drain frame 62 collapses toward the table (see FIG. 3). The crease 67 would thus make the present drape 10 more compatible with the frame 62 disclosed in the U.S. Pat. No. 4,936,836 patent.

Not all urology tables 61 include a drain frame 62 for receiving a drainage bag. Some urology tables have a built in pan (not shown) for collecting expelled fluids from the patient 32. For these type urology tables, it is preferable to use a modified version of the present drape 10 which does not have an attached drainage bag 20 and hose 23. Even without the bag 20 and hose 23, the general I-shape of the drape 10 still has advantages over the prior art T-shaped drapes, as previously discussed. For such a modified version of the present drape 10, it is particularly preferable that the screen filter 18 be securable over the pan (not shown) to insure that expelled fluid from the patient 32 passing through the lower fenestration 17 is in fact collected in the pan. The screen 18 could be secured over the pan by using two piece snaps 41 in a manner similar to that previously described or with any other suitable fasteners.

From the above disclosure of the general principles of the present invention and the preceding detailed description, those skilled in the art will readily appreciate changes and modifications which may be made without departure from the spirit of the present invention. Therefore, this invention is not intended to be limited except by the scope of the following claims.

What is claimed is:

1. A medical drape of the type useful for covering a patient on a table having a drain frame, the drape comprising:

a sheet having an upper sheet section with two side edges, and a lower sheet section with an upper fenestration and a lower fenestration formed therethrough, said lower fenestration having a perimeter substantially surrounding said lower fenestration formed by said lower sheet section, said perimeter being of sufficient surface area to extend beyond and drape over the drain frame when said lower fenestration is positioned within the drain frame;

a screen filter affixed to said lower sheet section and substantially covering said lower fenestration;

a drainage bag with an exit opening and an entrance opening, the entrance opening having a perimeter affixed to said lower sheet section around the perimeter of said lower fenestration; and a hose having one end attached to and in fluid communication with the exit opening of said drainage bag.

2. The drape of claim 1 wherein said lower sheet section has an upper portion with two side edges and a lower portion with two side edges, said upper portion being substantially narrower from side to side than said lower portion and said upper sheet section, thereby giving said drape a general I-shape when said drape is fully unfolded and spread out on a flat surface.

3. The drape of claim 2 wherein said upper fenestration is formed through the upper portion and said lower fenestration is formed through the lower portion of said lower sheet section.

4. The drape of claim 2 wherein the lower portion of said lower sheet section is provided with means for attaching said lower portion to a patient.

5. The drape of claim 4 wherein said attachment means is at least one piece of adhesive tape fixed along either side of said lower portion.

6. The drape of claim 2 wherein the lower portion of said lower sheet section has a bottom edge with attachment means fixed along said bottom edge.

7. The drape of claim 2 wherein the side to side width of the lower portion of said lower sheet section is comparable to the side to side width of said upper sheet section.

8. The drape of claim 2 wherein the lower portion of said lower sheet section is significantly wider from side to side than said upper sheet section.

9. The drape of claim 1 wherein a finger cot is fixed to said lower sheet section between said upper and said lower fenestrations.

10. The drape of claim 1 wherein means for holding a tube or cord to said drape is fixed to said lower sheet section.

11. The drape of claim 10 wherein said holding means includes at least one adhesive strip with a reapplyable cover strip.

12. The drape of claim 1 wherein both said lower sheet section and said upper sheet section are made of a 2-ply laminate comprising a layer of nonwoven fabric material and a layer of plastic film material.

13. The drape of claim 1 wherein at least said lower sheet section is made of a 2-ply laminate comprising a layer of nonwoven fabric material and a layer of plastic film material, said layer of plastic film material being textured to reduce glare from light reflected off of said plastic film layer.

14. The drape of claim 1 wherein said drape includes a collapsible drainage receptacle attached to and in fluid communication with the other end of said hose.

15. The drape of claim 14 wherein said drainage receptacle includes a hose connector which is removable from the other end of said hose and a vent for allowing the displacement of air as said drainage receptacle fills with liquid.

16. The drape of claim 14 wherein a jelling agent is contained within said drainage receptacle for turning liquids into a jell.

17. The drape of claim 1 including means for securing said lower sheet section to the drain frame while said drainage bag is positioned within the drain frame.

18. A medical drape comprising:

an upper sheet section having two side edges;

a lower sheet section with an upper fenestration and a lower fenestration formed therethrough, and having an upper portion with two side edges and a lower portion with two side edges, said upper portion being substantially narrower from side to side than said upper sheet section and said lower portion, thereby giving said drape a general I-shape when said drape is fully unfolded and spread out on a flat surface; and a screen filter affixed to said lower sheet section and disposed over said lower fenestration.

19. The drape of claim 18 wherein the side to side width of the lower portion of said lower sheet section is comparable to the side to side width of said upper sheet section.

20. The drape of claim 18 wherein the lower portion of said lower sheet section is significantly wider from side to side than said upper sheet section.

21. The drape of claim 18 wherein the lower portion of said lower sheet section has attachment means fixed along the side edges of said lower portion.

22. The drape of claim 18 wherein the lower portion of said lower sheet section has a bottom edge with attachment means fixed along said bottom edge.

23. A method for packaging a medical drape of the type useful for covering a patient on a table having a drain frame, the method comprising the steps of:

providing a drape with a sheet having a fenestration formed therethrough, the fenestration having a perimeter substantially surrounding the fenestration formed by the sheet, the perimeter being of sufficient surface area to extend beyond and drape over the drain frame when the fenestration is positioned within the drain frame, a screen filter affixed to the sheet and substantially covering the fenestration, and a drainage bag with an exit opening and an entrance opening, the entrance opening having a perimeter affixed to the sheet around the perimeter of the fenestration, and a hose having one end attached to the exit opening of the drainage bag for fluid communication therewith;

sterilizing the drape;

folding the drape to form a folded drape; and enclosing the folded drape in packaging material.

24. The method of claim 23 wherein said drape includes a collapsible drainage receptacle attached to and in fluid communication with the other end of said hose.

25. The method of claim 23 wherein said sheet is folded with said drainage bag being exposed outside thereof and with said hose coiled above said drainage bag.

26. The method of claim 25 wherein said folded drape is banded with a tape before being packaged.

27. The method of claim 25 wherein said drape includes a collapsible drainage receptacle attached to and in fluid communication with the other end of said hose, and said sheet is folded with said drainage receptacle collapsed above said coiled hose.

28. The method of claim 27 wherein said folded drape is banded with a tape before being packaged.

29. A method for deploying a sterile medical drape during a medical procedure comprising the steps of:

providing a packaged medical drape which includes a sheet with at least one fenestration formed therethrough, the fenestration having a perimeter substantially surrounding the at least one fenestration formed by the sheet, a screen filter affixed to the sheet and substantially covering the fenestration, and a drainage bag with an exit opening and an entrance opening having a perimeter affixed to the sheet and around the perimeter of the fenestration, and a hose having one end attached to the exit opening of the drainage bag for fluid communication therewith;

unpackaging the packaged medical drape; and dropping the hose and the drainage bag through a drain frame on a table supporting a patient and covering the patient with the drape sheet.

30. The method of claim 24 wherein said drape, before being packaged, is in a folded condition where said sheet is folded with said drainage bag being exposed outside thereof and with said hose coiled above said drainage bag.

31. The method of claim 30 wherein said folded drape is oriented with said drainage bag below said sheet and said hose below said drainage bag, said folded drape being positioned over the drain frame on a table before said hose and said drainage bag are dropped through the drain frame and a patient is covered with said drape sheet.

32. The method of claim 31 wherein said folded drape is banded with a piece of tape before being packaged, said tape being ripped in two before said hose and said drainage bag are dropped through the drain frame on a table.

33. The method of claim 24 wherein a patient is covered with said drape sheet before said hose and said drainage bag are dropped through a drain frame on a table.

34. The method of claim 24 wherein said packaged medical drape includes a collapsible drainage receptacle attached to and in fluid communication with the other end of said hose.

35. The method of claim 34 wherein said drape, before being packaged, is in a folded condition where said sheet is folded with said drainage bag being exposed outside thereof, with said hose coiled above said drainage bag and with said drainage receptacle collapsed above said coiled hose.

* * * * *

UNITED STATES PATENT AND TRADEMARK OFFICE
CERTIFICATE OF CORRECTION

PATENT NO. : 5,445,165
DATED : August 29, 1995
INVENTOR(S) : Robert C. Fenwick

It is certified that error appears in the above-indentified patent and that said Letters Patent is hereby corrected as shown below:

Column 11,

In claim 30, change "The method of claim 24..." to read --The method of claim 29...--.

Column 12,

In claim 33, change "The method of claim 24..." to read --The method of claim 29...--.

Column 12,

In claim 34, change "The method of claim 24..." to read --The method of claim 29...--.

Signed and Sealed this

Twenty-fifth Day of June, 1996

Attest:

BRUCE LEHMAN

Attesting Officer     Commissioner of Patents and Trademarks